United States Patent [19]

Kiefer et al.

[11] 4,229,351
[45] Oct. 21, 1980

[54] PROCESS FOR PRODUCING ALIPHATICALLY N-SUBSTITUTED MALEIMIDES

[75] Inventors: Jürg Kiefer, Reinach; Theobald Haug, Frenkendorf, both of Switzerland

[73] Assignee: Ciba-Geigy Corporation, Ardsley, N.Y.

[21] Appl. No.: 24,847

[22] Filed: Mar. 28, 1979

[30] Foreign Application Priority Data

Apr. 6, 1978 [CH] Switzerland ............... 3706/78

[51] Int. Cl.³ .............. C07D 207/448; C07D 207/452
[52] U.S. Cl. ..................... 260/326.26; 260/326.5 FM
[58] Field of Search ................ 260/326.26, 326.5 FM

[56] References Cited

U.S. PATENT DOCUMENTS

| | | | |
|---|---|---|---|
| 3,018,290 | 1/1962 | Sauers et al. | 260/326.3 |
| 3,839,358 | 10/1974 | Bargain | 260/326.26 |
| 4,130,564 | 12/1978 | Haug et al. | 260/326.26 |
| 4,138,406 | 2/1979 | Balas Falvy | 260/326.26 |

Primary Examiner—José Tovar
Attorney, Agent, or Firm—Luther A. R. Hall

[57] ABSTRACT

In the production of maleimides of the general formula I

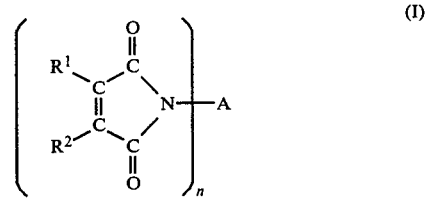

in which n is one of the numbers 1, 2 or 3, $R^1$ and $R^2$ are each a hydrogen atom or methyl, and A is an n-valent aliphatic, cycloaliphatic, aliphatic-cycloaliphatic or aliphatic-aromatic radical having up to 30 C atoms, by means of cyclising dehydration of a maleamic acid of the formula II

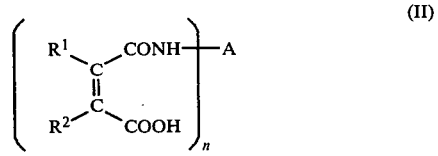

in which the acid amide group (s) is (are) attached to aliphatic or cycloaliphatic C atoms, in the presence of low-molecular dehydrating carboxylic anhydrides in an organic solvent and in the present of catalysts, there is advantageously used as solvent a polar aprotic solvent containing at least one N-lower-alkyl-substituted acid amide group in the molecule, or a solvent mixture containing an aprotic solvent of this type, and as catalyst a metal compound, and the cyclising dehydration is performed in the temperature range of 40° to 100° C.

6 Claims, No Drawings

PROCESS FOR PRODUCING ALIPHATICALLY N-SUBSTITUTED MALEIMIDES

The present invention relates to a process for producing aliphatically N-substituted maleimides in a specific polar aprotic solvent and in the presence of metal compounds as catalysts.

Several processes are already known for producing maleimides. The maleamic acids obtainable at an intermediate stage by reaction of maleic anhydride with primary mono- or polyamines are converted, as is known, by means of cyclising dehydration with the aid of carboxylic anhydride, in an organic solvent and in the presence of a catalyst, into the corresponding maleimides. Tertiary amines and metal salts have already been used as catalysts. The processes which have hitherto become known for producing maleimides give in some cases high yields with the use or aromatic amines; these processes are however less suitable for producing maleimides based on aliphatic amines, since only low yields are then obtained.

Thus, for example, in U.S. Pat. No. 3,018,290 the cyclising dehydration of maleimide acids in the presence of fairly large amounts of tertiary amines, such as triethylamine, is described. Although in this process aromatic maleimides are obtained in yields of up to 90%, the yields of aliphatic maleimides are in the range only of 17 to 35%.

Similarly, in the German Auslegeschrift No. 2,040,094 there is described the cyclising dehydration in the presence of a tertiary amine and additionally of a nickel salt. Dialkyl ketones are used as solvents. With this process too however the yields of aliphatic maleimides are considerably below those of the aromatic maleimides.

Furthermore, it is suggested in German Offenlegungsschrift No. 2,454,856 that the cyclising dehydration be performed in the presence of tertiary amines and of an alkaline-earth compound as catalyst. The production of aliphatically N-substituted maleimides is indeed not described in any Example, but it has been shown by copying this process for the production of aliphatically N-substituted maleimides that the yields obtained are only up to about 50%.

Finally, in German Offenlegungsschrift No. 2,715,503 there is described the production of maleimides in the presence only of tertiary amines as catalyst, with the cyclising dehydration being performed in a specific temperature range. In comparison with the yields obtained in the above-mentioned process, the yields of aliphatically N-substituted maleimides obtained in this case are somewhat higher, but on the basis of the melting point of 134°–136.5° C. given in Example 13 for N,N'-hexamethylene-bismaleimide it is recognised that the final product is still a highly contaminated substance.

It has now been found that aliphatically N-substituted maleimides are obtained in higher yields when the cyclising dehydration of the corresponding maleamic acids is performed in a specific polar aprotic solvent and in the presence of a metal compound. The process according to the invention has moreover the advantage that there are obtained purer final products which already satisfy the requirements with respect to the degree of purity for further processing, so that the costly recrystallisation of the final products is unnecessary.

The present invention relates therefore to a process for producing maleimides of the general formula I

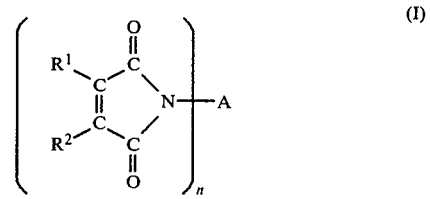

in which n is one of the numbers 1, 2, or 3, $R^1$ and $R^2$ are each a hydrogen atom or methyl, and A is an n-valent aliphatic, cycloaliphatic, aliphatic-cycloaliphatic or aliphatic-aromatic radical having up to 30 C atoms, by means of cyclising dehydration of a maleamic acid of the formula II

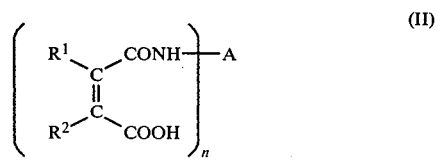

in which the acid amide group(s) is (are) attached to aliphatic or cycloaliphatic C atoms, in the presence of low-molecular dehydrating carboxylic anhydrides in an organic solvent and in the presence of catalysts, which process comprises using as solvent a polar aprotic solvent containing at least one N-lower-alkyl-substituted acid amide group in the molecule, or a solvent mixture containing an aprotic solvent of this type, and a metal compound as catalyst; and performing the cyclising dehydration in the temperature range of 40° to 100° C., preferably 60° to 80° C.

As maleimides of the formula II in the process according to the invention, there are preferably used compounds of the formula IIa

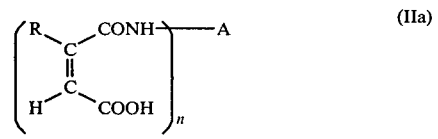

in which n is a number 1, 2 or 3, R is a hydrogen atom or methyl, preferably hydrogen, A is an n-valent aliphatic radical having up to 30 C atoms, and the acid amide group(s) is (are) attached to aliphatic C atoms.

The mono- or polymaleamic acids used as starting substances for the process according to the invention can be produced by known processes which are described in detail in the above-cited patent specifications with reference to relevant literature.

As starting materials for the process according to the invention, there are particularly advantageously used however those mono- or polymaleamic acids which have been obtained by reaction of maleic or 2-methylmaleic anhydride with primary aliphatic mono- or polyamines of the formula III

(H₂N)ₙ̄A      (III)

in the special polar aprotic solvent. This procedure enables the corresponding maleamic acids to be produced without in this stage of the process the reaction solution having to be cooled, and furthermore the maleamic acids are obtained in excellent quality. The maleamic acids produced in this manner do not therefore need to be isolated from the reaction solution, and they can thus be converted directly, by cyclising dehydration, into the maleimides of the formula I.

The procedure in practice comprises dissolving the maleic anhydride in the special aprotic solvent, and then adding dropwise the amine, likewise dissolved in the solvent, in such a manner that the reaction solution warms up to about 60° to 90° C. If by way of comparison chloroform is used as the solvent, the reaction solution has to be intensively cooled, or otherwise the maleamic acids are obtained in a highly contaminated form. For producing the maleamic acids of the formula II or IIa, maleic, 2-methylmaleic or 2,3-dimethylmaleic anhydride is reacted with the respective mono- or polyamine in such a quantity ratio that there are 1.0 to 1.5 mols of maleic anhydride to 1 equivalent of amine.

In the process according to the invention, there are used in particular maleamic acids of the formula IIa in which n is 1 or 2, and A is an aliphatic radical containing up to 20 C atoms, especially up to 12 C atoms.

To be included among the maleamic acids of the formula II or IIa, which can be used in the process according to the invention, are also such compounds wherein the aliphatic radical A contains double bonds, or is interrupted by bridge members, such as —O—, —S—, —SO$_2$—, =N—, —NR$_1$— (R$_1$=alkyl or phenyl), —PO= or —Si(R$_1$)$_2$—. The aliphatic radical A can also contain a phenylene radical or cycloaliphatic radical or an N-heterocyclic radical, such as a dihydrouracil radical, particularly a hydantoin radical, provided that all maleamic acid groups in the formula II are attached to aliphatic C atoms.

The aliphatic radical A in the formula II, IIa or III, or the phenylene or N-heterocyclic radicals optionally contained in the aliphatic radical A, can also contain substituents which do not disadvantageously influence the imide formation. The following may be mentioned as examples of such substituents: halogen atoms, alkylenes, alkoxyls, —NO$_2$ and —SO$_3$H.

As monoamines of the formula III which can be used for producing the maleamic acids of the formula II, there may be mentioned in particular: methylamine, allylamine, butylamine, iso-butylamine, hexylamine, nonylamine, dodecylamine, cyclohexylamine, aminomethylcyclohexane and benzylamine.

Suitable diamines of the formula III which may be mentioned are: ethylenediamine, tetramethylenediamine, hexamethylenediamine, octamethylenediamine, decamethylenediamine, dodecamethylenediamine, 2,2-dimethyl-1,3-diaminopropane, 2,5-dimethyl-1,5-diaminoheptane, 2,5-dimethyl-1,6-diaminohexane, 2,5-dimethyl-1,7-diaminoheptane, 3,3,5-trimethyl-1,6-diaminohexane, 1,2-bis-(3-aminopropoxy)-ethane, 3-methoxy-1,6-diaminohexane, H$_2$N(CH$_2$)$_3$O(CH$_2$)$_3$NH$_2$, H$_2$N(CH$_2$)$_3$S(CH$_2$)$_3$NH$_2$, H$_2$N-C$_2$H$_4$-S-C$_2$H$_4$-NH$_2$, H$_2$N(CH$_2$)$_3$N(CH$_3$) (CH$_2$)$_3$NH$_2$, m-xylylenediamine, p-xylylenediamine N,N'-bis-(3-aminopropyl)-5,5-dimethylhydantoin, 4,4'-diaminodicyclohexylmethane, 3,3'-dimethyl-4,4'-diaminodicyclohexylmethane, 4,4'-diaminodicyclohexyl ether, 4,4'-diaminodicyclohexylsulfone, 4,4'-diaminodicyclohexylisopropane, 1,2-bis-(aminomethyl)-cyclohexane, 1,3bis-(aminomethyl)-cyclohexane and 1,4-bis-(aminomethyl)-cyclohexane.

Examples of trivalent amines are:

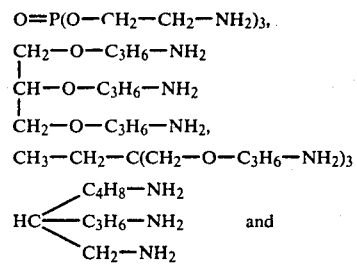

and 1,8-diamino-4-aminomethyl-octane.

The following may be mentioned as examples of polar aprotic solvents which contain at least one N-lower-alkyl-substituted acid amide group in the molecule: dimethylacetamide, diethylacetamide, tetramethylurea, hexamethylphosphoric acid triamide, N-methylcaprolactam and N-methylpyrrolidone, or mixtures of these solvents. It is also possible to use for the process according to the invention solvent mixtures which contain up to the extent of 50 percent by volume an organic solvent which is different from the above-defined polar aprotic solvent, and which is inert under the reaction conditions. There may be mentioned as organic inert solvents of this type: acetone, dioxane, methylene chloride, toluene, ethyl acetate, acetonitrile, nitromethane and tetrahydrofuran.

The amount of solvent to be used in the process is not critical provided that the amount is sufficient to dissolve therein the starting materials at least partially. In general, the process is performed with 20 to 60 percent by weight solutions, relative to the amount of starting materials.

Suitable metal compounds, which can be used as catalysts in the process according to the invention, are both inorganic metal compounds and organic metal compounds, for example the salts of inorganic or organic acids, and also phenolates, alcoholates or the metal-complex compounds. The compounds of the following metals have proved to be particularly effective: Li, Mg, Ni, Co, Cu, Mn, Zn, Sn, Ti, Tl, Fe, Pb, V and La. Compounds of the metals Co, Zn, Pb, Mn, V, Ti and La are preferably used.

Acetic anhydride is advantageously used as the low-molecular dehydrating carboxylic anhydride. The appropriate anhydride is used in an amount of at least 1.2 mols per mol of maleamic acid group. There are in general used larger amounts, which are in the order of 1.5 to 2 mols per mol of maleamic acid group.

EXAMPLE 1

In a reaction vessel, 9.80 g (0.10 mol) of maleic anhydride is dissolved in 25 ml of hexamethylphosphoric triamide. To this solution is added dropwise, with stirring, 5.80 g (0.05 mol) of hexamethylenediamine dissolved in 25 ml of hexamethylphosphoric triamide, and 1.0 g of cobalt naphthenate and 20.4 g (0.20 mol) of acetic anhydride are subsequently introduced into the reaction vessel. The solution is then heated for 2 hours at 70°–80° C., and afterwards cooled to about 10° C., in the course of which almost colourless crystals precipitate. To complete crystallisation, an addition of 100 ml of ice water is made to the crystal suspension already present. The yield after filtration and drying is 11.8 g of nearly colourless crystals having a melting point of 138°–139° C., and these crystals are, according to the analytical data, hexamethylene-bis-maleimide (in the following denoted as "HBMI");

Yield: 86% of theory.

EXAMPLES 2 and 3 as well as Comparison 1 and 2

The procedure is carried out in these Examples in the manner described in Example 1 except that as solvent there is used, in place of hexamethylphosphoric triamide, acetonitrile, dioxane, N-methylpyrrolidone or tetramethylurea. Table 1 shows the solvent used, the yield and the melting point (as criterion of purity).

TABLE 1

| Examples | Solvent | Yield of "HBMI" | Melting point °C. |
|---|---|---|---|
| comparison 1 | acetonitrile | — | 154–158 |
| comparison 2 | dioxane | — | 153–160 |
| 2 | N-methyl-pyrrolidone | 75% | 137–139 |
| 3 | tetramethyl-urea | 75% | 138–140 |

In the comparisons 1 and 2, amounts of 0.9 g and 2.0 g, respectively, of a crystalline substance are indeed isolated; however, the melting point indicates that these substances are not "HBMI". Although acetonitrile and dioxane too are aprotic solvents, they are unsuitable for the process according to the invention for obtaining for example "HBMI". The Examples 2 and 3 clearly show the favourable effect of the special polar aprotic solvents in the formation of maleimides aliphatically substituted on the nitrogen atom.

EXAMPLE 4

50 ml of dimethylacetamide, 15.5 g (0.05 mol) of hexamethylene-bis-maleamic acid and 1.0 g of cobalt naphthenate are introduced into a reaction vessel, and the suspension is heated to 70°–80° C., whereupon a clear solution forms. To this is added dropwise, with stirring, 20.4 g (0.20 mol) of acetic anhydride. The solution is heated for 2 hours at 70°–80° C., and then cooled to about 10° C., with almost colourless crystals already precipitating. An addition of about 100 ml of ice water is subsequently made and, after filtration and drying, the yield is 11.4 g of "1,6-HBMI" having a melting point of 136°–138° C.;

Yield: 83% of theory.

EXAMPLES 5–10

These bis-maleimides are all produced by the following process:

A solution of 0.05 mol of the diamine in 25 ml of dimethylacetamide is added dropwise in a reaction vessel, at room temperature, to a solution of 0.10 mol of maleic anhydride in 25 ml of dimethylacetamide; there is then added 1 g of cobalt naphthenate and the temperature is raised to 60°–80° C.; 0.20 mol of acetic anhydride is added dropwise into the vessel, and the contents of the flask are held for about a further 2 hours at 70°–80° C.; the temperature is subsequently lowered to about 10° C., and 50–100 ml of water is added to the formed crystal suspension. The resulting bis-maleimide is filtered off and dried. Table 2 contains the diamines used, the melting points of the bis-maleimides and the yields. The analytical data are in each case in agreement with the assumed structure.

TABLE 2

| Ex.-amples | Diamine NH$_2$—A—NH$_2$ —A— | Bis-maleimides Melting point °C. | Yield [% of theory] |
|---|---|---|---|
| 5 | —C$_2$H$_4$— | 189–190 | 77.5 |
| 6 | —C$_3$H$_6$— | 165–167 | 80.1 |
| 7 | —C$_4$H$_8$— | 200–201 | 78.5 |
| 8 | —CH$_2$—C(CH$_3$)$_2$—C$_2$H$_4$—CH(CH$_3$)—CH$_2$ | 88–102 | 80.0 |
| 9 | —C$_2$H$_4$—S—C$_2$H$_4$— | 121–122 | 82.5 |
| 10 | 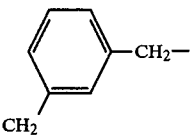 | 123–125 | 79 |

EXAMPLE 11

15.5 g (0.10 mol) of N-allyl-maleamic acid is dissolved in 50 ml of dimethylacetamide in a reaction vessel; 1.0 g of cobalt naphthenate is then added to the solution and this is heated to about 70°–80° C.; 20.4 g (0.20 mol) of acetic anhydride is added, and the solution is held for about a further two hours at about 80° C. The solution is subsequently cooled to about 10° C., and 100 ml of water is added. A light-brown crystal suspension is formed, and the crystals are filtered off and dried. The filtrate is extracted twice with 50 ml of chloroform each time; the organic phases are then combined, and the crystals thus obtained are combined with the 1st crystal fraction. The yield is 9.9 g of light-brown crystals which have a melting point of 41°–43° C. and which, according to all analytical data, are N-allyl-maleimide. Yield 72% of theory.

EXAMPLE 12

17.1 g (0.10 mol) of N-n-butylmaleamic acid is dissolved in 50 ml of dimethylacetamide in a reaction vessel; 1.0 g of cobalt naphthenate and 20.4 g (0.20 mol) of acetic anhydride are added, and the solution is heated at 80°–90° C. for 2.5 hours. After cooling, 100 ml of water is added to the solution; the organic phase is then separated, and the aqueous phase is extracted twice with 50 ml of chloroform each time, and the combined, dried chloroformic solution is added to the organic phase previously separated. The chloroform is distilled off to leave behind 16.5 g of a yellow oil; distillation then yields 12.3 g of a colourless pure liquid, b.p. 50°–53° C./6.67 Pa, which, according to analytical data, is -n-butylmaleimide.

Yield: 80.4% of theory.

EXAMPLE 13

A solution of 14.3 g (0.10 mol) of n-nonylamine in 25 ml of dimethylacetamide is added dropwise in a reaction vessel to a solution of 9.8 g (0.10 mol) of maleic anhydride in 25 ml of dimethylacetamide. To the clear solution is added 0.5 g of cobalt naphthenate, and 20.4 g (0.20 mol) of acetic anhydride is added dropwise to the solution within about 10 minutes; the whole is heated to 70°–80° C. and this temperature is held for a further 2 hours. It is then lowered to about 10° C., and about 50 ml of water is added to the crystal suspension. The yield after filtration and drying is 17.3 g of almost colourless crystals which have a melting point of 49.5–50° C. and which, according to the analytical data, are N-n-nonyl-maleimide; yield 77.6% of theory.

EXAMPLE 14

25 ml of dimethylacetamide, 25 ml of dimethylformamide and 15.6 g (0.05 mol) of hexamethylene-bis-maleamic acid are placed into a reaction flask, and the temperature is raised to 60°–65° C., in the course of which a clear solution is formed. To this is added 1.0 g of tetrabutyl-orthotitanate as well as 20.4 g (0.20 mol) of acetic anhydride. The solution is heated for 3 hours at about 60° C. and is then cooled to 10° C., during which time crystals are already precipitating. An addition of about 100 ml of ice water is subsequently made and, after filtering and drying, the yield is 10.2 g of "1,6-HBMI" having a melting point of 139°–140° C.

Yield: 74% of theory.

EXAMPLE 15

Example 14 is repeated with the difference that now 25 ml of dioxane is used in place of 25 ml of dimethylformamide. After processing in the manner described in Example 14, there is obtained "1,6-HBMI" in 69%.

Yield with a melting point of 140°–141° C.

EXAMPLES 16 to 22 (variations of catalyst)

If the procedure is carried out under the same conditions as in Example 1 except that, instead of cobalt naphthenate, equal amounts of other metal compounds are used as catalyst, there are obtained the yields given in Table 3.

TABLE 3

| Example | Catalyst | Yield [% of theory] | Melting point [°C.] |
|---|---|---|---|
| 16 | Tl-(I)-acetate | 65 | 139–141 |
| 17 | Pb-octoate | 75 | 138–140 |
| 18 | Zn-octoate | 74 | 136–138 |
| 19 | La-nitrate | 75 | 138–140 |
| 20 | tetrabutyl titanate | 83 | 138–141.5 |
| 21 | V-(III)-acetylacetonate | 75 | 137–141 |
| 22 | Mn-(II)-acetate | 73 | 140–142 |

COMPARATIVE EXAMPLES

Comparison 3

In a reaction vessel, 15.8 g (0.05 mol) of 1,6-hexamethylene-bis-maleamic acid in 50 ml of dimethylacetamide is heated to about 70° C., and 20.4 g (0.20 mol) of acetic anhydride is then added. The resulting clear solution is heated for 7.5 hours at 70°–80° C.; it is subsequently cooled to about 15° C., and 100 ml of water is added. The yield after filtering and drying is 3.0 g of brownish crystals having a melting point of 135°–138° C.

Yield of "HBMI" is 22% of theory.

A comparison with Example 4 shows the surprisingly favourable effect of metal salt on the imide formation.

COMPARISON 4

31.20 g (0.10 mol) of hexamethylenebismaleamic acid, 50 ml of acetone, 5.05 g (0.05 mol) of triethylamine and 1.0 g of nickel acetate are placed into a reaction vessel. This suspension is heated to boiling, and 30.6 g (0.30 mol) of acetic anhydride is added with stirring. The suspension is refluxed for 140 minutes, in the course of which it gradually changes into a clear solution; this is subsequently cooled to about 10° C., and 100 ml of water is added. The crystals which have precipitated are filtered off and dried to yield 9.80 g of "1,6-HBMI" with a melting point of 136°–139° C.; yield 36% of theory.

This comparison shows that the yield is substantially lower using the process according to German Auslegeschrift No. 2,040,094, and that, surprisingly, triethylamine has an unfavourable effect on the formation of "1,6-HBMI".

COMPARISON 5

31.2 g (0.10 mol) of hexamethylenebismaleamic acid, 50 ml of dimethylacetamide, 1 g of calcium acetate and 3.52 g (0.034 mol) of triethylamine are placed into a reaction vessel. The solution is heated to about 55° C., and 32.6 g (0.32 mol) of acetic anhydride is added dropwise with stirring. The solution is subsequently heated for a further 2 hours at about 60° C., and afterwards cooled to about 30° C. There is then added 100 ml of water, and a light-brown dispersion is formed. The crystals which have precipitated are filtered off and dried to obtain 14.2 g of "1,6-HBMI" having a melting point of 139°–141° C.

Yield 51.4% of theory.

The comparison shows that the process described in German Offenlegungsschrift No. 2,454,856 is likewise only capable of producing low yields of hexamethylenebismaleimide.

EXAMPLE 23

A solution of 0.1 mol of benzylamine in 25 ml of dimethylacetamide is added dropwise, at room temperature, in a reaction vessel to a solution of 0.1 mol of citraconic anhydride dissolved in 25 ml of dimethylacetamide; 1 g of cobalt naphthenate is then added and the temperature is raised to 60° C; 0.2 mol of acetic anhydride is introduced into the vessel, and the contents of the flask are maintained at 60° C. for about 2 hours; the temperature is subsequently lowered to about 10° C., and 50–100 ml of water is added dropwise. The resulting crystal suspension is filtered off and dried. The yield is 14.70 g of fine light-beige crystals having a melting point of 57°–58.5° C. and which are, according to MS and NMR spectrum, with certainty N-benzylcitracone amide yield 73.2% of theory.

EXAMPLE 24

A solution of 0.1 mol of cyclohexylamine in 25 ml of dimethylacetamide is added dropwise in a reaction vessel, at room temperature, to a solution of 0.1 mol of dimethylmaleic anhydride dissolved in 25 ml of dimethylacetamide; an addition of 1 g of cobalt naphthenate is then made, and, likewise at room temperature, 0.2 mol of acetic anhydride is added dropwise into the vessel. The solution meanwhile warms up to 40° C. After the dropwise addition, stirring is continued for one further hour at room temperature; the temperature is subsequently lowered to about 10° C., and 100 ml of water is added. There is formed a fine suspension; this is then filtered, and the crystalline substance is dried to thus obtained 15.0 g of white crystals which have a melting point of 91.5°–93° C. and which, according to the analytical data, are N-cyclohexyl-dimethylamaleimide.

yield: 72.4% of theory.

EXAMPLE 25

Example 24 is repeated with the exception that 0.1 mol of n-butylamine is used instead of cyclohexylamine. Processing as in Example 24 yields 15.1 g of white crystals which have a melting point of 93°–94° C. and which, according to the analytical data, are N-n-butyl-dimethylmaleimide.

yield: 83.4% of theory.

EXAMPLE 26

Production of

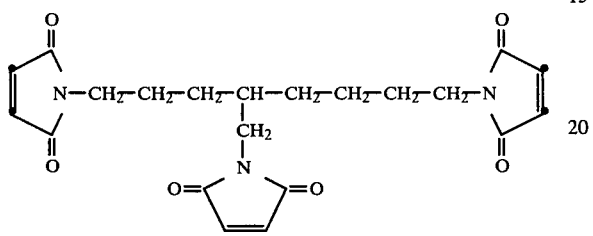

A solution of 0.05 mol of 1,8-diamino-4-aminomethyloctane in 25 ml of dimethylacetamide is added dropwise in a reaction vessel, at room temperature, to a solution of 0.15 mol of maleic anhydride dissolved in 25 ml of dimethylacetamide; 1.5 g of cobalt naphthenate is then added, and the temperature is raised to 60°–70° C.; 0.3 mol of acetic anhydride is added dropwise, and the reaction mixture is held for 2 hours at this temperature. It is subsequently cooled to 10° C. and 200 ml of water is added. A yellow viscous oil precipitates. The aqueous solution is distilled off, and the oil remaining is dissolved in methanol. The solution is concentrated in a rotary evaporator until the weight remains constant. The yield is 18.4 g of yellow, viscous oil which, according to the analytical data (MS, NMR spectrum), is with certainty the desired imide.

yield: 89.10% of theory.

What is claimed is:

1. An improved process for producing maleimides of formula I

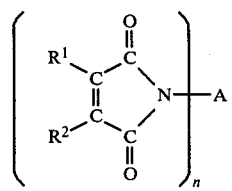
(I)

in which n is one of the numbers 1, 2 or 3, $R^1$ and $R^2$ are independently hydrogen or methyl, A is an n-valent aliphatic, cycloaliphatic, aliphatic-cycloaliphatic or aliphatic-aromatic radical having up to 30 carbon atoms by means of the cyclizing dehydration at a temperature range of 40° to 100° C. of a maleamic acid of the formula II

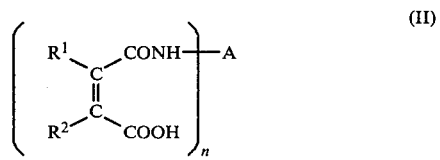
(II)

in which the acid amide group is attached to aliphatic or cycloaliphatic C atoms in the presence of a low-molecular weight dehydrating carboxylic anhydride in an organic solvent and in the presence of a catalyst wherein the improvement comprises employing an effective amount of a catalyst which is an organic or inorganic compound of a metal selected from the group consisting of Li, Mg, Ni, Co, Cu, Mn, Zn, Sn, Ti, Tl, Fe. Pb, V and La, and carrying out the reaction in a sufficient amount of a polar aprotic solvent selected from the group consisting of dimethylformamide, dimethylacetamide, diethylacetamide, tetramethylurea, hexamethyl phosphoric acid triamide, N-methylcaprolactam, N-methylpyrrolidone and mixtures thereof, to give at least a partial solution of the starting materials.

2. A process according to claim 1, wherein the employed maleamic acids of the formula II are compounds of the formula IIa

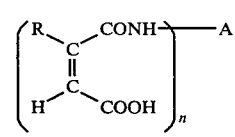
(IIa)

in which n is one of the numbers 1, 2 or 3, R is a hydrogen or methyl, A is an n-valent aliphatic radical having up to 30 C atoms, and the acid amide group is attached to aliphatic C atoms.

3. A process according to claim 2, wherein there are used maleamic acids of the formula IIa in which n is 1 or 2, and A is an aliphatic radical containing up to 20 C atoms.

4. A process according to claim 1, wherein the solvent used is a solvent mixture containing up to the extent of 50 percent by volume an organic inert solvent which is different form the aprotic polar solvent.

5. A process according to claim 1, wherein the cyclising dehydration is performed in the temperature range of 60° to 80° C.

6. A process according to claim 1 or 2, wherein there are used maleamic acids of the formula II or IIa, which are obtained by reaction of maleic or 2-methylmaleic anhydride with primary aliphatic mono- or polyamines of the formula III $(H_2N)_n A$ (III)

in a polar aprotic solvent containing at least one polar aprotic solvent selected from the group consisting of dimethylformamide, dimethylacetamide, diethylacetamide, tetramethylurea, hexamethyl phosphoric acid triamide, N-methylcaprolactam, N-methylpyrrolidone and mixtures thereof, or in a solvent mixture containing an aprotic solvent from this group.

* * * * *